United States Patent [19]

Savelli et al.

[11] 4,232,666
[45] Nov. 11, 1980

[54] MEDICAL BREATHING APPARATUS

[75] Inventors: Aulo Savelli; Francesco Grianti; Giovanni Arcozzi; Leonardo Di Bari, all of Pesaro, Italy

[73] Assignee: D G T S.r.l., Pesaro, Italy

[21] Appl. No.: 20,718

[22] Filed: Mar. 15, 1979

[30] Foreign Application Priority Data

Mar. 16, 1978 [IT] Italy .................. 21273 A/78

[51] Int. Cl.³ ............................................ A61M 16/00
[52] U.S. Cl. ........................ 128/203.25; 128/204.21; 128/205.11; 128/205.24
[58] Field of Search ............... 128/145.8, 145.6, 145.5, 128/142 R, 142.2, 142.3, 142.5, 142.7, 188, 209, 210, 204.21, 205.11, 205.24, 203.25

[56] References Cited

U.S. PATENT DOCUMENTS

| 2,121,311 | 6/1938 | Anderson et al. | 128/145.8 |
| 3,434,471 | 3/1969 | Liston | 128/145.8 |
| 3,859,994 | 1/1975 | Almquist et al. | 128/142.3 |
| 3,905,363 | 9/1975 | Dudley | 128/145.8 |
| 3,910,270 | 10/1975 | Stewart | 128/145.8 |
| 4,026,283 | 5/1977 | Banjavich et al. | 128/142.3 |
| 4,137,912 | 2/1979 | O'Neill | 137/505.13 X |

Primary Examiner—Henry J. Recla

[57] ABSTRACT

A breathing apparatus having a pair of inspiration manifolds in series disposed with interposition of flow regulating means. A pressure stabilizer and governor is disposed upstream of the pair of inspiration manifolds. The pressure stabilizer employs a constant volume reservoir connected to a source of fluid under pressure and contains a variable volume chamber connected to the first inspiration manifold. A detector is provided for detecting the volume changes of the variable volume member and controlling flow in the inspiration circuit. An expiration circuit is directly connected to the atmosphere with interposition of flow regulating and intercepting means. Provision is made for coupling the expiration circuit to a source of vacuum.

6 Claims, 4 Drawing Figures

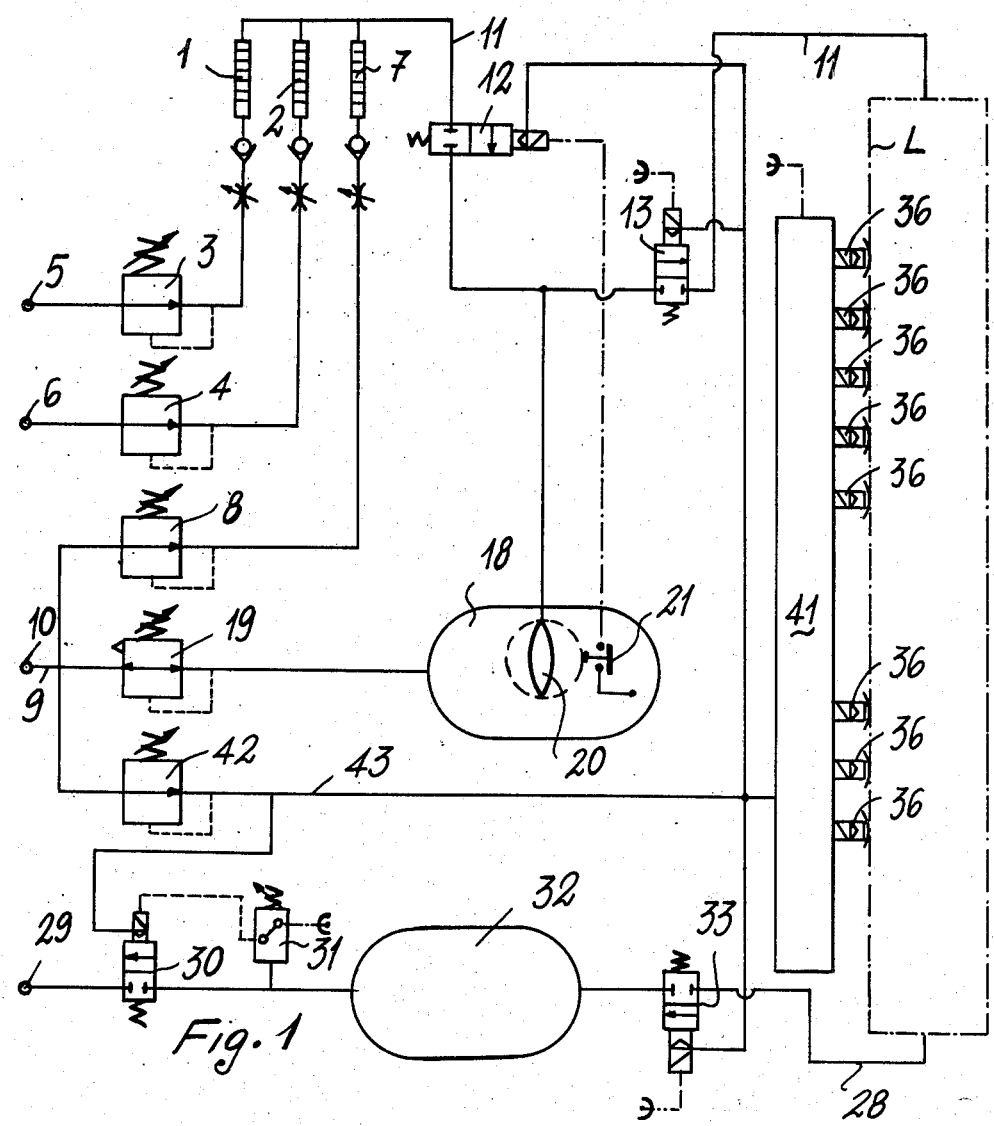
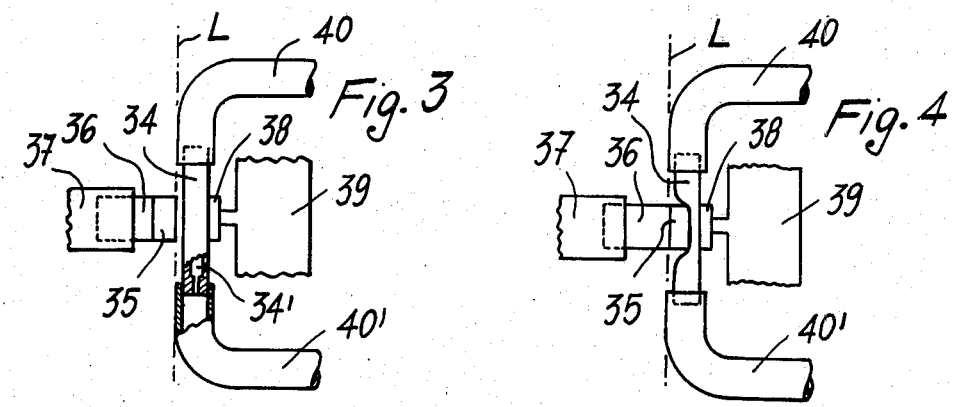
Fig. 1
Fig. 3
Fig. 4

MEDICAL BREATHING APPARATUS

BACKGROUND OF THE INVENTION

The present invention relates to a rate of flow controlled automatic, medical breathing apparatus particularly suitable for reanimation and anaesthesia rooms.

The conventional rate of flow controlled automatic, medical breathing apparatuses—also known as lung ventilators—respiratory gas flow depending on the clinical and physical conditions of the patient.

Such breathing apparatuses are conventionally provided with a relatively low pressure source, of the order maximally allowed by the respiratory passages of the patient, and with an inner resistance of the apparatus which varies according to the difference between a theoretical preselected value and a real measured value, both values relating to one or more flow parameters, as disclosed—for example—in the U.S. Pat. No. 3,741,208.

A drawback of this solution resides in the flow instability resulting as a consequence of the occasional changes of the patient's resistance. This is due to the feeble pressure head. It follows that necessity causes an effort to be made to reset the flow by correcting the error by means of devices operated by a step motor which squeeze or open a resilient pipe, usually a silicone rubber pipe, through which the respiratory gas flows.

Since the operating times of such devices are very long in relation to the exigencies of the respiratory cycle (the operating times are of the order of 1/10 second while the total inspiration times are of the order of 2/10 or 3/10 second) the resulting errors are so excessive that effective control of the inspiratory curve is not obtained.

The correction of the error, and hence of the rate of flow curve, further depends on the accuracy of the same rate of flow measurement. The accuracy of such measurement depends upon the accuracy of the transducer used which, as is known, is systematically degraded by the necessity of sterilization of the transducer. It follows that an incorrect measurement is directly reflected on the flow pattern.

A further conventional technique used in the rate of flow controlled breathing apparatus resides in the provision of a high pressure source with elevated internal constant resistance. Thus, when chstable. The drawback of such a type of high pressure ventilators resides essentially in the difficulty of keeping the primary high pressure steady when substantially large drawings of respiratory gas occur. As a consequence, there is a loss in the rate of flow control. High pressure stability and hence stability of the flow can be obtained by using a large high pressure reservoir, but such a large reservoir in turn causes a drawback; variations of the respiratory gas composition imposed at the input are displaced at the output with a too long delay. On the other hand, it is practically impossible to maintain the high pressure steady in a feeding source formed by a bellows subjected to the pressure long, strong and of difficult adjustment and/or an excessively small volume of utilizable respiratory gas would be obtained from the bellows.

In the conventional breathing apparatuses of the above described type the inspiration curve is determined by the structure of the same apparatus and said structure cannot be modified so as to adapt the breathing apparatus to the required various clinical exigencies.

SUMMARY OF THE INVENTION

An object of the invention is to provide a rate of flow controlled automatic, medical breathing apparatus which embodies the advantages but avoids the drawbacks of the conventional apparatuses and, in particular, which allows, due to the controlled stability of the flow effective changes in the pattern of the inspiration rate of flow according to curves selected at will by the operator depending on the clinical and pathological necessities of the patient.

The rate of flow controlled automatic, medical breathing apparatus, according to the invention, comprises a first inspiration circuit for the inspiration of the desired respiratory gas mixture and a second expiration circuit and is essentially characterized in that said inspiration circuit comprises a pair of in series disposed manifolds, a pressure stabilizer and governor upstream disposed relative to said pair of manifolds and flow regulating means interposed between the manifolds of said pair, said second expiration circuit being directly connected to the atmosphere with interposition of flow intercepting means.

The novel features which are considered as characteristic of the invention are set forth in particular in the appended claims. The apparatus itself, however, both as to its construction and its mode of operation, together with additional features and advantages thereof, will be better understood upon perusal of the following detailed description with reference to the accompanying drawings.

BRIEF DESCRIPTION OF THE DRAWINGS

FIG. 1 shows a diagram of the breathing apparatus;

FIGS. 3 and 4 show, enlarged, a particular of a valve respectively in open and closed position.

DESCRIPTION OF THE PREFERRED EMBODIMENT

Figure 2:
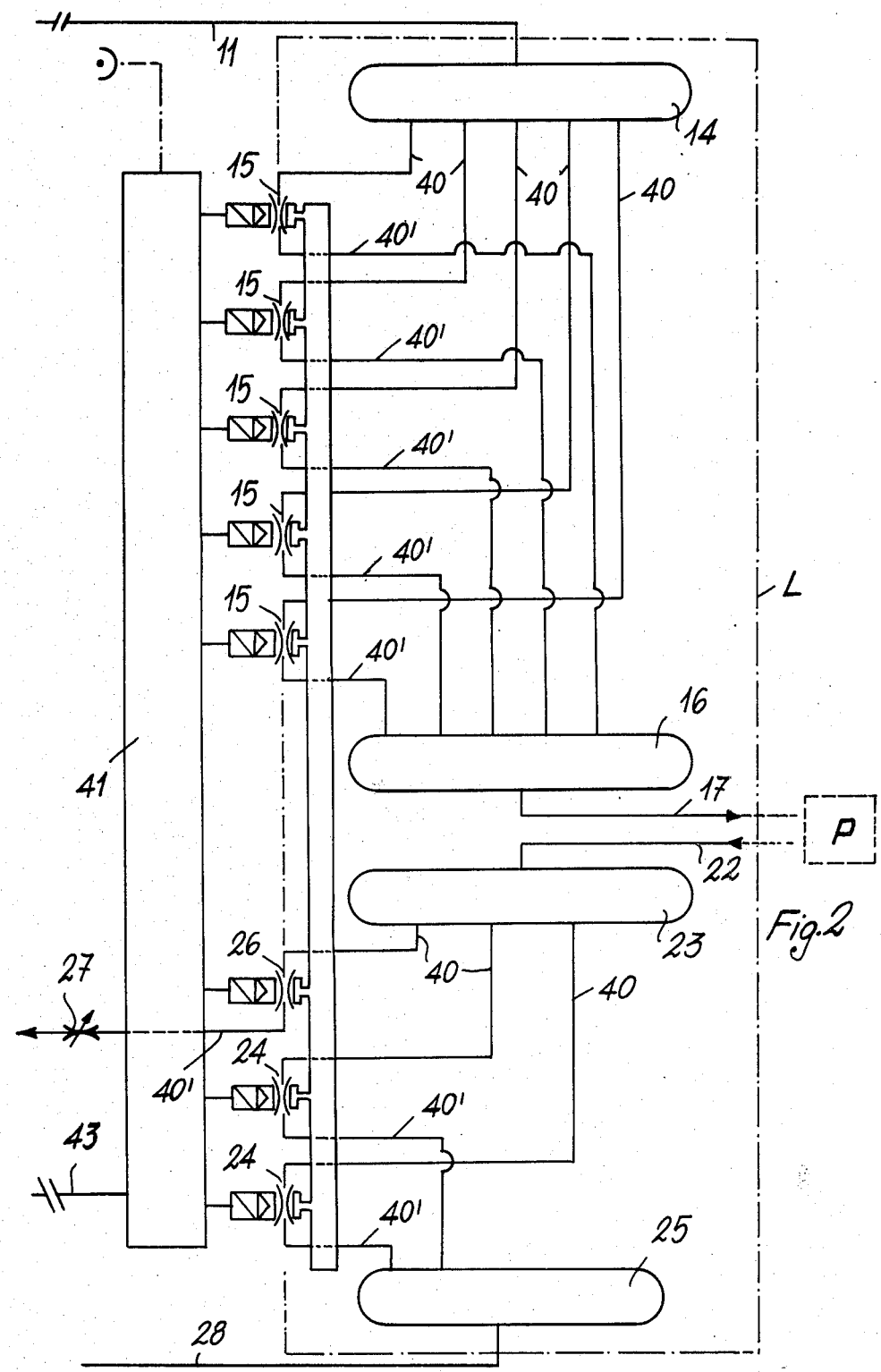
FIG. 2 shows, diagrammatically and enlarged, the removable part for sterilization purpose delimited by a dashed line in FIG. 1.

With reference to the figures, the breathing apparatus comprises two adjustable flowmeters 1 and 2 respectively connected, through pressure regulating valves 3 and 4, each to a source 5 and 6 of a suitable anaesthetic and/or curative substance, for example nitrous oxide and oxygen. A third flowmeter 7 is connected, through a pressure regulating valve 8, to a conduit 9 derived from an air compressed source 10. From the flowmeters 1,2 and 7 the respiratory gas mixture is fed to a common conduit 11, making part of the first inspiration circuit, along which two normally closed pneumatic intercepting valves 12 and 13 are provided, and which conduit flows in a first inspiration manifold 14 in series connected, through a plurality of valves 15 hereinafter better described, to a second inspiration manifold 16 connectable to a patient P through an inspiration conduit 17.

A pressure stabilizer and governor in the form of a constant volume reservoir 18 is connected, through an exhaust type pneumatic pressure regulating valve 19, to the air compressed conduit 9. A small balloon 20, made of very soft rubber of the type normally used in the hospitals, is disposed inside said reservoir 18 and connected to the conduit 11 between the valves 12 and 13. Inside the reservoir 18 there is also positioned a microswitch 21 closely disposed relative to the balloon 20 to detect the volume increase and decrease thereof and connected to the pneumatic valve 12 to close said valve when said microswitch is switched from the closed to the open position due to the volume increase of said balloon and to open the same valve 12 when the volume of the same balloon 20 decreases.

The second expiration circuit comprises an expiration conduit 22 connected to the patient P and flowing into a first expiration manifold 23 in series connected, through a plurality of valves 24 of the same type of the valves 15, to a second expiration manifold 25. The first manifold 23 is also connected to the atmosphere by means of a conduit 40 provided with an intercepting valve 26 and an adjustable throttle 27.

A vacuum source 29 is connected to the second manifold 25 through a conduit 28 along which there are provided a first normally closed pneumatic valve 30, a vacuometer 31, a vacuum reservoir 32 and a second normally closed pneumatic valve 33.

As shown in particular in the FIGS. 2, 3 and 4, the valves 15, 24 and 26 are each formed by a silicone rubber or other suitable soft material pipe 34 adapted to be squeezed (FIG. 4) or opened (FIG. 3) between a pad 35 carried by the upper end of a piston 36 of a pneumatic cylinder 37 and a counterplate 38 secured to a stationary element 39. Each pipe 34 is connected at one end to a related conduit 40 coming from the manifolds 14 and 23 and at the other end, through a gauged throttle member 34', to a related conduit 40' directed towards the manifolds 16 and 25. As above stated, one of the conduits 40 is connected to the input of the intercepting valve 26 the output of which is connected, through a conduit 40', to the adjustable throttle 27 flowing into atmosphere.

The valves 15, 24 and 26 have been chosen of the type described to make said valves and related manifolds easily separable from the remaining of the breathing apparatus for as easy and quick sterilization thereof. As shown in the figures, the valves 15, 24 and 26 and the manifolds 14, 16 and 23, 25 all make part of a block, delimited in the figures by a dashed line L, which can be easily disassembled and subjected in its whole to autoclave sterilization.

In the embodiment shown the pistons 36 are controlled by any conventional mechanical or electronic programmer 41 so as to change the inspiration rate of flow during the inspiration time according to necessities imposed by the various pathological conditions of the patient. This is obtained by causing through the programmer 41 the opening and/or closing of one or more valves 15 and by properly controlling also the valves 24, 26 and the adjustable throttle 27 during the expiration phase.

The members 34' of the valves 15 and 24 are of very easy replacement for a quick substitution thereof with other differently gauged members, this in order to change the average inner resistance of the breathing apparatus which, as known, defines the flow steadiness in relation to the changes of the outer resistance opposed by the patient.

The valves 15 and 24 can be in any desired number and in a further embodiment not shown said valves can be substituted with a single variable throttle valve, such as pin valves mechanically controlled by a cam or electronically controlled by a motor, screw and encoder.

A pressure regulating valve 42 provided in a conduit 43 derived from the air compressed conduit 9 pneumatically controls the valves 12, 13, 30 and 33 and the pneumatic members 36, 37 of the programmer 41.

In the operation, the adjustable flowmeters 1, 2 and 7, respectively fed by sources 5, 6 and 10 through the regulating valves 3, 4 and 8, deliver the mixture of the respiratory gas to the manifold 14. From the manifold 14, through the valves 15 partially or totally opened by the programmer 41 according to necessities, the mixture is let into the manifold 16 from which it is supplied to the patient P through the conduit 17. During the expiration phase the valves 15 will of course remain closed.

For the reasons explained in the preface of the present description, it is of importance that the pressure in the manifold 14 be kept constant and without surging from the desired value. An important feature of the present invention is reservoir 18 connected to the air compressed conduit 9 through the exhaust type pressure regulating valve 19, for maintaining the pressure constant. By adjusting the knob of said regulating valve 19, the pressure in the reservoir 18 can be increased and decreased at will.

By increasing or decreasing the pressure in the reservoir 18 there will be a corresponding increase or decrease of the flow through the valves 15 and hence an increase or decrease of the current volume, i.e. the respiratory gas volume supplied to the patient P during each breathing act. During the expiration phase (valves 15 closed) the balloon 20 will increase its volume and during the inspiration phase said volume will decrease. If the volume change of the balloon 20 is small relative to the volume of the reservoir 18 also the pressure change in the same reservoir will be insignificant and consequently the pressure change in the manifold 14 will also be insignificant.

The division of the small volume of the balloon 20 from the bigger one of the reservoir 18 allows good pressure stability in the manifold 14 without inhibiting a quick and controllable change in the mixture composition of the respiratory gas fed to the manifold 14, when such a mixture change is desired and carried out by operating on the flowmeters 1, 2 and 7.

A good pressure stability could be simply obtained, as a matter of fact, by positioning a reservoir having a suitably large volume along the conduit 11 since said large volume will not be affected by the fact that a continuous flow is fed by the flowmeters while a discontinuous flow is drawn from the manifold 14. Such a large volume of the reservoir would however cause a considerable delay between the time in which the mixture composition is changed upstream of the reservoir and the time in which the new mixture is ready to be delivered to the patient downstream of the same reservoir.

The balloon 20 pratically contains a volume of respiratory gas just enough to assure one breathing act. Said volume of respiratory gas is subjected to the pressure of the fluid outside the balloon and the pressure in the conduit 11 will be always the same as the one inside the reservoir 18 thus assuring a constant pressure during the full inspiration act (less 1/100 or 2/100 of atm. and until the balloon is completely collapsed).

The small maximum volume of the balloon 20, as above stated enough to assure one breathing act, further allows the quick washing of the same balloon with the modified mixture and it will be therefore immediately ready to deliver the new modified mixture.

Should the balloon expand beyond a preselected value the balloon will operate the microswitch 21 to close the valve 12, which valve 12 will re-open as soon as the microswitch is switched back by the decreasing volume of the same balloon 20.

The respiratory gas to be inspired by the patient P exits from the manifold 16 through the conduit 17 and returns, as expired air, through the conduit 22 to the manifold 23 and therefrom to the atmosphere through the valve 26. The valve 26 allows a natural expiration by discharging to the atmosphere with a more or less flowing out depending on the adjustment, according to necessities, of the throttle 27.

In some pathological cases it may be advisable to apply to the respiratory passages also a moderate and controllable suction effect. Should this be the case, the valve 26 is closed and the valves 24 are opened, according to a preselected program imposed by the programmer 41, so as to connect the manifold 23 to the manifold 25. The desired vacuum degree in the manifold 25 will be maintained by the vacuum reservoir 32 conjointly with the vacuometer 31 and the valve 30.

The valves 12, 13, 30 and 31, all normally closed, will provide to intercept the related circuits should the electric energy and/or the air pressure be off. The valve 26, normally open, will in such a case put the respiratory passages of the patient P in free communication with the atmosphere.

From the foregoing the flexibility and adaptability of the breathing apparatus according to the invention clearly appear, since:

(a) by changing the pressure inside the reservoir 18 one may change the flow and, therefore, the current volume by leaving unchanged the remaining;

(b) by changing the opening sequence of the valves 15 the same results as (a) are obtained with the further possibility of changing at will the pattern of the inspiratory rate of flow (inspiration curves);

(c) by changing only the duration of the inspiration phase a variation of the current volume can be obtained; and (d) by changing the gauged throttle members 34' in series disposed to the valves 15 (inner resistances) the same results may also be obtained.

It is, indeed, by appropriately combining these possibilities that a great flexibility and stability of the breathing apparatus can be obtained.

With a small pressure and a low inner resistance, for example, one may obtain the same current volume as with a high pressure and a high inner resistance. In the first case, however, the flow will feel the change of the inner resistance (patient-pressure generator), while in the second case the flow will remain steady when the outer resistance (flow generator) changes.

Further to the above, by suitably changing and combining pressure, time, inner resistance and program (above points a, b, c and d) it will be possible to ventilate any type of patients, in reanimation as well as in anaesthesia, babies and adults in any clinical condition.

Still further, other than the inspiration and expiration ratio and the exclusion or not of the suction phase (which is possible also with the conventional breathing apparatuses), it is possible to change at will the placing of an eventual suction phase in any desired time of the expiration phase. More particularly, the expiration phase can be divided into three times T1, T2 and T3 wherein during T1 the valves 15 and 24 are closed and the valve 26 is open (natural breathing); during T2 the valves 15 and 26 are closed and, by opening the valves 24 according to a desired program, vacuum is applied (negative pressure); and during T3 the same conditions as T1 are repeated.

T1, T2 and T3 are variable at will and independent between them and from the duration of the inspiration phase.

The possibility to place T2 between the two times T1 and T3 of the natural and controlled breathing is of importance since it allows to apply the correct negative pressure according to the different clinical exigencies.

In the embodiment shown the second expiration circuit comprises a pair of manifolds 23 and 25 since there is provided a vacuum source 29 for applying a negative pressure to the patient but said pair of manifolds and the related parts 24, 28–33 can be omitted by directly connecting the expiration conduit 22 to the atmosphere with interposition of the intercepting valve 26 and adjustable throttle 27.

The particular construction of the breathing apparatus according to the invention allows the use of a same signal generated by a conventional pressure transducer (not shown) disposed along the inspiration or expiration conduits 17 or 22, respectively, to carry out different functions usually obtained in the conventional apparatuses by means of non-return and/or calibrated valves. Said functions are, for example, the following;

to maintain a preselected minimum positive pressure (PEEP) in the respiratory circuit of the patient by simply closing the intercepting valve 26;

to operate a conventional optical and/or acoustical alarm of maximum pressure when the pressure in the conduits 17 and 22 exceed a preselected value: in this case it is also possible to provide for the immediate closure of the valves 15 and opening of the valve 26 (pressure cycled);

to actuate the TRIGGER function, i.e. to immediately start an inspiration phase when the patient, due to an inspiration attempt, causes a very faint depression in the conduits 17 and 22: in this case the same valve 26 acts as a non-return valve by closing at a preselected pressure which can also be lower than the atmospheric pressure.

Without further analysis, the foregoing reveals the gist of the present invention and other conventional devices usually employed in the breathing apparatuses have not been herein described for a better understanding of said gist. It should further pointed out that the programmer 41, of mechanical or electronic type as stated in the description, can be realized in any desired manner as it is well known to the men skilled in the art.

What we claim is:

1. A rate of flow controlled automatic medical breathing apparatus comprising:
  means for supplying a respiratory gas mixture including first conduit means wherein said mixture flows;
  valve means in said first conduit means for controlling the flow of said respiratory gas mixture into the apparatus;
  a first inspiration manifold downstream of said valve means;
  a pressure stabilizer and governor means interposed in said first conduit means between said valve means and said first inspiration manifold;
  second conduit means downstream of said first inspiration manifold, comprising at least two parallel conduits and having first flow regulating means in each of said parallel conduits;

a second inspiration manifold downstream of said first inspiration manifold, wherein said parallel conduits of said second conduit means are joined;

inspiration means connectable to a patient and including an inspiration conduit connected to said second inspiration manifold;

expiration means connectable to a patient and including an expiration conduit; and second flow regulating means in said expiration conduit;

controlling means for controlling said first and second flow regulating means in said second conduit means and said expiration conduit so as to change the inspiration flow and expiration flow for a respiration cycle according to necessities imposed by the various pathological conditions of a patient;

and wherein said pressure stabilizer and governor means further comprises:

a constant volume reservoir;

supply means for supplying a fluid at a preselected pressure into said constant volume reservoir;

a variable volume member inside said reservoir, the interior of said variable volume member being isolated from said constant volume reservoir and connected to said first conduit means downstream of said valve means; and detecting and control means for detecting the volume of said variable volume member and controlling said valve means to prevent flow therethrough when a predetermined increased volume is detected and permit flow therethrough when a predetermined decreased volume is detected.

2. A breathing apparatus as defined in claim 1, wherein said variable volume member is an inflatable balloon and said detecting means is a microswitch closely disposed relative to said inflatable balloon for detecting the volume increase and decrease thereof and connected to said first valve means for closing and opening said latter means depending on the inflated state of said inflatable balloon.

3. A breathing apparatus as defined in claim 2, wherein said inflatable balloon has a maximum volume corresponding to the current volume of the respiratory gas mixture to be supplied to the patient during each breathing act.

4. A rate of flow controlled automatic medical breathing apparatus comprising;

means for supplying a respiratory gas mixture including first conduit means wherein said mixture flows;

valve means in said first conduit means for controlling the flow of said respiratory gas mixture into the apparatus;

a first inspiration manifold downstream of said valve means;

a pressure stabilizer and governor means interposed in said first conduit means between said valve means and said first inspiration manifold;

second conduit means downstream of said first inspiration manifold, comprising at least two parallel conduits and having first flow regulating means in each of said parallel conduits;

a second inspiration manifold downstream of said first inspiration manifold, wherein said parallel conduits of said second conduit means are joined;

inspiration means connectable to a patient and including an inspiration conduit connected to said second inspiration manifold;

expiration means connectable to a patient and including an expiration conduit; and second flow regulating means in said expiration conduit;

controlling means for controlling said first and second flow regulating means in said second conduit means and said expiration conduit so as to change the inspiration flow and expiration flow for a respiration cycle according to necessities imposed by the various pathological conditions of a patient;

and wherein said first flow regulating means in said parallel conduits and said second flow regulating means in said expiration conduit further comprise a plurality of valves responsive to said controlling means, each of said plurality of valves comprising;

a resilient pipe connected in said respective conduits having a gauged throttle member therein; and relatively movable members responsive to said controlling means for squeezing said resilient pipe.

5. A rate of flow controlled breathing apparatus, as claimed in claim 4, wherein said controlling means for controlling said relatively movable members comprises any conventional programmer means, and wherein said gauged throttle members are replaceable and interchangeable.

6. A breathing apparatus as defined in claim 1 or 4 also comprising a vacuum source, wherein said expiration means comprises:

a first expiration manifold;

a second expiration manifold connected in series relative to said first expiration manifold in said expiration conduit, said second flow regulating means being interposed between said first and second expiration manifolds; and third flow regulating means responsive to said controlling means for connecting said first expiration manifold to the atmosphere;

said second expiration manifold being connected to said vacuum source and said control means controlling said second and third flow regulating means such that said second expiration manifold is connected to said vacuum source when said first expiration manifold is disconnected to atmosphere and said second expiration manifold is disconnected from said vacuum source when said first expiration manifold is connected to atmosphere.

* * * * *